(12) United States Patent
Hass et al.

(10) Patent No.: US 8,497,094 B2
(45) Date of Patent: Jul. 30, 2013

(54) PREVENTION AND TREATMENT OF COMPLEMENT-ASSOCIATED EYE CONDITIONS

(75) Inventors: Philip Hass, Moss Beach, CA (US); Yin Jianping, Foster City, CA (US); Kenneth Katschke, Jr., Millbrae, CA (US); Micah Steffek, San Francisco, CA (US); Christian Wiesmann, Brisbane, CA (US); Menno Van Lookeren Campagne, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/554,787

(22) Filed: Jul. 20, 2012

(65) Prior Publication Data

US 2013/0052685 A1 Feb. 28, 2013

Related U.S. Application Data

(63) Continuation of application No. 13/189,301, filed on Jul. 22, 2011, now Pat. No. 8,268,310, which is a continuation of application No. 12/154,466, filed on May 22, 2008, now Pat. No. 8,007,791.

(60) Provisional application No. 60/939,791, filed on May 23, 2007.

(51) Int. Cl.
*C12P 21/06* (2006.01)
*C12N 5/10* (2006.01)
*C12N 15/63* (2006.01)
*C07H 21/00* (2006.01)

(52) U.S. Cl.
USPC .......... 435/69.1; 435/326; 435/328; 435/337; 435/348; 435/358; 435/252.3; 435/254.2; 435/320.1; 536/23.1; 536/23.53

(58) Field of Classification Search
None
See application file for complete search history.

(56) References Cited

U.S. PATENT DOCUMENTS

| | | | |
|---|---|---|---|
| 6,410,708 B1 | 6/2002 | Ashkenazi et al. | |
| 6,472,520 B2 | 10/2002 | Fisher | |
| 6,569,992 B1 | 5/2003 | LaFleur et al. | |
| 6,642,353 B1 | 11/2003 | McConnell et al. | |
| 6,838,554 B2 | 1/2005 | Ashkenazi et al. | |
| 7,192,589 B2 | 3/2007 | Ashkenazi et al. | |
| 7,211,400 B2 | 5/2007 | Ashkenazi et al. | |
| 7,282,565 B2 | 10/2007 | Goddard et al. | |
| 7,419,663 B2 | 9/2008 | Ashkenazi et al. | |
| 8,007,791 B2 | 8/2011 | Hass et al. | |
| 8,372,403 B2 * | 2/2013 | An et al. | 424/145.1 |
| 2002/0081293 A1 | 6/2002 | Fung et al. | |
| 2004/0152105 A1 | 8/2004 | Vogt et al. | |
| 2005/0197285 A1 | 9/2005 | Rosen et al. | |
| 2006/0233803 A1 | 10/2006 | Ashkenazi et al. | |
| 2007/0190054 A1 | 8/2007 | Ashkenazi et al. | |
| 2009/0214538 A1 | 8/2009 | Fung et al. | |

FOREIGN PATENT DOCUMENTS

| | | |
|---|---|---|
| WO | WO 99/27098 | 3/1999 |
| WO | WO 99/40100 | 8/1999 |
| WO | WO 99/42133 | 8/1999 |
| WO | WO 99/46281 | 9/1999 |
| WO | WO 00/12703 | 3/2000 |
| WO | WO 00/36102 | 6/2000 |
| WO | WO 00/37638 | 6/2000 |
| WO | WO 00/53749 | 9/2000 |
| WO | WO 00/53758 | 9/2000 |
| WO | WO 01/04311 | 1/2001 |
| WO | WO 01/36432 | 5/2001 |
| WO | WO 01/40466 | 6/2001 |
| WO | WO 02/00690 A2 | 1/2002 |
| WO | WO 02/08284 | 1/2002 |
| WO | WO 2004/022594 | 3/2004 |
| WO | WO 2006/042329 | 4/2006 |
| WO | WO 2006/071856 | 7/2006 |
| WO | WO 2007/056227 | 5/2007 |
| WO | WO 2007/087384 | 8/2007 |
| WO | WO 2009/011461 | 9/2009 |

OTHER PUBLICATIONS

Aderem, et al., "Mechanisms of phagocytosis in macrophages", Annu. Rev. Immnuol., 17: 593-623, (1999).
Akif, U., et al., The Annals of Thoracic Surgery, 74(2): 355.362 (2002).
Arrate, et al., "Cloning of human junctional adhesion molecule 3 (JAM3) and its identification as the JAM2 counter-receptor", The journal of biological chemistry, vol. 276, No. 49, pp. 45826-45832, (2001).
Attwood, "The Babel of Bioinformatics", Science 290: 471-473, (2000).
Bora, P., et al., The Journal of Immunology, 174(1): 491.497 (2005).
Brown, "Complement receptors, adhesion and phagocytosis", Infectious agents and disease, 1: 63-70, (1992).
Carroll, "The complement system in regulation of adaptive immunity", Nature Immunology, vol. 5, No. 10, pp. 981-986, (2004).
Casset, et al., "A peptide mimetic of an anti-CD4 monoclonal antibody by rational design", BBRC, 307: 198-205, (2003).
Database Genebank (Apr. 24, 2001), "Human Pro 1868 Protein" Database Accession No. AAB80272, XP002448361.
Edwards, et al., "Complement factor H polymorphism and age-related macular degeneration", Science, vol. 308, pp. 421-424, (2005).
Haines, et al., "Complement factor H variant increases the risk of age-related macular degeneration", Science, vol. 308, pp. 419-421, (2005).
Harboe, M., et al., Clinical and Experimental Immunology, 138(3): 439.446 (2004).
Holers, et al., "The evolution of mouse and human complement C3-binding proteins: divergence of form but conservation of function", Immunology Today, vol. 13, No. 6, pp. 231-236, (1992).
Janssen, et al., "Structural insights into the central complement component C3", Molecular Immunology, 44: 3-10, (2007).

(Continued)

*Primary Examiner* — Jeffrey Stucker
*Assistant Examiner* — Stephen Gucker
(74) *Attorney, Agent, or Firm* — Bonny Yeung; Victoria L. Boyd; Arnold & Porter LLP

(57) ABSTRACT

The invention concerns the prevention and treatment of complement-associated eye conditions, such as choroidal neovascularization (CNV) and age-related macular degeneration (AMD), by administration of Factor D antagonists.

9 Claims, 8 Drawing Sheets

OTHER PUBLICATIONS

Katschke, et al., "A novel inhibitor of the alternative pathway of complement reverses inflammation and bone destruction in experimental arthritis", Brief Definitive Report, vol. 204, No. 6, pp. 1319-1325, (2007).

Kim, et al., "Characterization of monoclonal antibody specific to the Z39Ig protein, a member of immunoglobulin superfamily", Immunology Letters, 99: 153-161, (2005).

Klein, et al., "Complement factor H polymorphism in age-related macular degeneration", Science, vol. 308, pp. 385-389, (2005).

Langnaese, et al., "Cloning of Z39Ig, a novel gene with immunoglobulin-like domains located on human chromosome XI", BBA, pp. 522-525, (2000).

Lee, et al., "Z39Ig is expressed on macrophages and may mediate inflammatory reactions in arthritis and atherosclerosis", Journal of Leukocyte biology, vol. 80, pp. 922-928, (2006).

MacCallum, et al., "Antibody-antigen interactions: Contact analysis and binding site topography", J. Mol. Biol., 262:,'732-745, (1996).

Petrukhin, K., et al., Expert Opinion on Therapeutic Targets, 11(5): 625.639 (2007).

Pyz, et al., "C-type lectin-like receptors on myeloid cells", Annals of Medicine, 38: 242-251, (2006).

Ross, et al., "Membrane complement receptors specific for bound fragments of C3", Advances in Immunology, vol. 37, pp. 217-267, (1985).

Rudikoff, et al., "Single amino acid substitution altering antigen-binding specificity", PNAS, vol. 79, pp. 1979-1983, (1982).

Skolnick, et al., "From genes to protein structure and function: novel applications of computational approaches in the genomic era", Trends in Biotech.,18:34-39, (2000).

Strausberg, et al., "Generation and initial analysis of more than 15,000 full-length human and mouse cDNA se uences", PNAS, vol. 99, No. 26, es 16899-16903 (2002).

Stuart, et al., "Phagocytosis: Elegant complexity", Immunity, vol. 22, pp. 539-550, (2005).

Tanhehco, E., et al., Transplantation Proceedings, 31(5): 2168.2171 (1999).

Taylor, et al., "Macrophage receptors and immune recognition", Annu. Rev. Immunol., 23: 901-944, (2005).

Taylor, et al., "Pattern recognition receptors and differentiation antigens define murine myeloid cell heterogeneity ex vivo", Eur. J. Immunol., 33: 2090-2097, (2003).

Thurman, et al., "The central role of the alternative complement pathway in human disease", The Journal of Immunology, 176: 1305-1310, (2006).

Tsukita, et al., "Multifunctional strands in tight junctions", Nature Reviews, vol. 2, pp. 285-293, (2001).

Underhill, et al., Phagocytosis of microbes: Complexity in action, Annu. Rev. Immunol., 20: 825-852, (2002).

Walker, et al., Z39Ig is co-expressed with activation macrophage genes Biochimica et Biophysica Acta, 1574: 387-390, (2002).

Walport, "Complement: first of two parts", Advances in Immunology, N. Eng. J. Med., vol. 344, No. 14, pp. 1058-1066, (2001).

Wu, et al., "Humanization of a murine monoclonal antibody by simultaneous optimization of framework and CRD residues", JMB, 294: 151-162, (1999).

* cited by examiner

Sequence of antibody 20D12

Light chain sequence 20D12:

MGWSCIILFLVATATGVHSDIVMTQSQKFMSTSVGDRVSVTCKASQNVDTD
VAWFQQKPGQSPRGLIYSASSRYSGVPDRFTGSGSGTDFTLTISNVQSEDL
AEYFCQQYNNYPLTFGSGTKVEIKRTVAAPSVFIFPPSDEQLKSGTASVVCL
LNNFYPREAKVQWKVDNALQSGNSQESVTEQDSKDSTYSLSSTLTLSKADY
EKHKVYACEVTHQGLSSPVTKSFNRGEC

Heavy chain sequence 20D12

MGWSCIILFLVATATGAYAQVQLQQSGAELVKPGASVKLSCKASGYTFTSY
YMYWVKERPGQGLEWIGEINPTNGGTNFNEKFKSKATLTVDTSSNTAYMQ
LSSLTSEDSAVYYCAREGGFAYWGQGTLVTVSAASTKGPSVFPLAPSSKS
TSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHY
TQKSLSLSPGK

Human complement factor D (NP_038487.1)

```
  1 MHSSVYFVAL VILGAAVCAA QPRGRILGGQ EAAAHARPYM
 41 ASVQVNGTHV CGGTLLDEQW VLSAAHCMDG VTDDDSVQVL
 81 LGAHSLSAPE PYKRWYDVQS VVPHPGSRPD SLEDDLILFK
121 LSQNASLGPH VRPLPLQYED KEVEPGTLCD VAGWGVVTHA
161 GRRPDVLHQL RVSIMNRTTC NLRTYHDGVV TINMMCAESN
201 RRDTCRGDSG SPLVCGDAVE GVVTWGSRVC GNGKKPGVYT
241 RVSSYRMWIE NITNGNMTS
```

Donor tissues used in the studies

| Genentech # | Age | Sex | AMD Stage | Dissection notes |
|---|---|---|---|---|
| 1 | 78 | F | 3 | Foveal scar, few macular drusen FS |
| 1A | 78 | F | | No drusen evident |
| 2 | 85 | M | 4 | Geographic Atrophy GA |
| 2A | 85 | F | | No drusen evident |
| 3 | 87 | F | 4 | Fibrovascular scar in fovea FS |
| 3A | 87 | F | | No drusen evident |
| 4 | 76 | M | 4 | Geographic Atrophy GA |
| 4A | 74 | M | | Two small drusen present |
| 5 | 81 | F | 3+ | Moderate macular drusen MD |
| 5A | 81 | M | | No drusen evident |
| 6 | 84 | F | 3 | Numerous macular drusen MD |
| 6A | 86 | M | | No drusen evident |
| 7 | 83 | F | 4 | Fibrovascular scar in fovea FS |
| 7A | 83 | M | | No drusen evident |
| 8 | 72 | M | 4 | Foveal scar, Moderate macular drusen FS |
| 8A | 71 | F | | No drusen evident |
| 9 | 81 | F | 4 | Foveal scar, Moderate macular drusen FS |
| 9A | 83 | M | | No drusen evident |
| 10 | 77 | M | 3 | Numerous macular drusen MD |
| 10A | 78 | M | | No drusen evident |

☐ Geographic atrophy
☐ Foveal scar
☐ Stage 3 AMD

PREVENTION AND TREATMENT OF COMPLEMENT-ASSOCIATED EYE CONDITIONS

CROSS-REFERENCE TO RELATED APPLICATIONS

This application is a continuation of U.S. application Ser. No. 13/189,301, filed Jul. 22, 2011 (now U.S. Pat. No. 8,268, 310), which is a continuation of U.S. application Ser. No. 12/154,466, filed May 22, 2008 (now U.S. Pat. No. 8,007, 791) which is a non-provisional application filed under 37 CFR 1.53(b)(1), claiming priority under 35 USC §119(e) and the benefit of U.S. Provisional application No. 60/939,791 filed May 23, 2007, the contents of which are incorporated herein by reference in their entireties.

FIELD OF THE INVENTION

The present invention concerns the prevention and treatment of complement-associated eye conditions, such as choroidal neovascularization (CNV) and age-related macular degeneration (AMD).

BACKGROUND OF THE INVENTION

The complement system is a complex enzyme cascade made up of a series of serum glycoproteins, that normally exist in inactive, pro-enzyme form. Two main pathways, the classical and the alternative pathway, can activate complement, which merge at the level of C3, where two similar C3 convertases cleave C3 into C3a and C3b.

Macrophages are specialist cells that have developed an innate capacity to recognize subtle differences in the structure of cell-surface expressed identification tags, so called molecular patterns (Taylor, et al., *Eur J Immunol* 33, 2090-2097 (2003); Taylor, et al., *Annu Rev Immunol* 23, 901-944 (2005)). While the direct recognition of these surface structures is a fundamental aspect of innate immunity, opsonization allows generic macrophage receptors to mediate engulfment, increasing the efficiency and diversifying recognition repertoire of the phagocyte (Stuart and Ezekowitz, *Immunity* 22, 539-550 (2005)). The process of phagocytosis involves multiple ligand-receptor interactions, and it is now clear that various opsonins, including immunoglobulins, collectins, and complement components, guide the cellular activities required for pathogen internalization through interaction with macrophage cell surface receptors (reviewed by Aderem and Underhill, *Annu Rev Immunol* 17, 593-623 (1999); Underhill and Ozinsky, *Annu Rev Immunol* 20, 825-852 (2002)). While natural immunoglobulins encoded by germline genes can recognize a wide variety of pathogens, the majority of opsonizing IgG is generated through adaptive immunity, and therefore efficient clearance through Fc receptors is not immediate (Carroll, *Nat Immunol* 5, 981-986 (2004)). Complement, on the other hand, rapidly recognizes pathogen surface molecules and primes the particle for uptake by complement receptors (Brown, *Infect Agents Dis* 1, 63-70 (1991)).

Complement consists of over 30 serum proteins that opsonize a wide variety of pathogens for recognition by complement receptors. Depending on the initial trigger of the cascade, three pathways can be distinguished (reviewed by (Walport, *N Engl J Med* 344, 1058-1066 (2001)). All three share the common step of activating the central component C3, but they differ according to the nature of recognition and the initial biochemical steps leading to C3 activation. The classical pathway is activated by antibodies bound to the pathogen surface, which in turn bind the C1q complement component, setting off a serine protease cascade that ultimately cleaves C3 to its active form, C3b. The lectin pathway is activated after recognition of carbohydrate motifs by lectin proteins. To date, three members of this pathway have been identified: the mannose-binding lectins (MBL), the SIGN-R1 family of lectins and the ficolins (Pyz et al., *Ann Med* 38, 242-251 (2006)) Both MBL and ficolins are associated with serine proteases, which act like C1 in the classical pathway, activating components C2 and C4 leading to the central C3 step. The alternative pathway contrasts with both the classical and lectin pathways in that it is activated due to direct reaction of the internal C3 ester with recognition motifs on the pathogen surface. Initial C3 binding to an activating surface leads to rapid amplification of C3b deposition through the action of the alternative pathway proteases Factor B and Factor D. Importantly, C3b deposited by either the classical or the lectin pathway also can lead to amplification of C3b deposition through the actions of Factors B and D. In all three pathways of complement activation, the pivotal step in opsonization is conversion of the component C3 to C3b. Cleavage of C3 by enzymes of the complement cascades exposes the thioester to nucleophilic attack, allowing covalent attachment of C3b onto antigen surfaces via the thioester domain. This is the initial step in complement opsonization. Subsequent proteolysis of the bound C3b produces iC3b, C3c and C3dg, fragments that are recognized by different receptors (Ross and Medof, *Adv Immunol* 37, 217-267 (1985)). This cleavage abolishes the ability of C3b to further amplify C3b deposition and activate the late components of the complement cascade, including the membrane attack complex, capable of direct membrane damage. However, macrophage phagocytic receptors recognize C3b and its fragments preferentially; due to the versatility of the ester-bond formation, C3-mediated opsonization is central to pathogen recognition (Holers et al, *Immunol Today* 13, 231-236 (1992)), and receptors for the various C3 degradation products therefore play an important role in the host immune response.

C3 itself is a complex and flexible protein consisting of 13 distinct domains. The core of the molecule is made up of 8 so-called macroglobulin (MG) domains, which constitute the tightly packed α and β chains of C3. Inserted into this structure are CUB (C1r/C1s, Uegf and Bone mophogenetic protein-1) and TED domains, the latter containing the thioester bond that allows covalent association of C3b with pathogen surfaces. The remaining domains contain C3a or act as linkers and spacers of the core domains. Comparison of C3b and C3c structures to C3 demonstrate that the molecule undergoes major conformational rearrangements with each proteolysis, which exposes not only the TED, but additional new surfaces of the molecule that can interact with cellular receptors (Janssen and Gros, Mol Immunol 44, 3-10 (2007)).

Age-related Macular Degeneration (AMD) is the leading cause of blindness in the elderly worldwide. AMD is characterized by a progressive loss of central vision attributable to degenerative and neovascular changes in the macula, a highly specialized region of the ocular retina responsible for fine visual acuity. Recent estimates indicate that 14 million persons are blind or severely visually impaired because of AMD. The disease has a tremendous impact on the physical and mental health of the geriatric population and their families and is becoming a major public health burden.

New discoveries, however, are beginning to provide a clearer picture of the relevant cellular events, genetic factors, and biochemical processes associated with early AMD. The complement Factor H gene is the first gene identified in multiple independent studies that confers a significant genetic risk for the development of AMD. Thus, three separate groups reported that a tyrosine-histidine polymorphism at amino acid 402 of Factor H is associated with the development of AMD (Klein et al., Science 308:385-389 (2005); Haines et al., Science 308:419-421 (2005); and Edwards et al., Science 308:421-424 (2005)). It has been suggested that impaired alternative pathway inhibition by the disease-associated Factor H allele either causes or contributes significantly to the development of AMD (Thurman and Holers, *J Immunol* 176: 1305-1310 (2006)).

SUMMARY OF THE INVENTION

In one aspect, the present invention concerns a method for the prevention or treatment of a complement-associated eye condition comprising administering to a subject in need an effective amount of a Factor D antagonist.

In various embodiments, the subject in need is a mammal, such as a human, and the Factor D antagonist is selected from the group consisting of anti-Factor D antibodies and fragments thereof, binding polypeptides, peptides, and non-peptide small molecules.

In a preferred embodiment, the Factor D antagonist is an antibody or an antibody fragment. In various embodiments, the antibody may bind to the active site of Factor D, or may bind an epitope including active site residues of Factor D.

Specific antibodies within the scope of this invention include, without limitation, antibodies 20D12, 31A9, 25A1 and 32H12, and variants thereof. In a preferred embodiment, the antibody or antibody fragment binds essentially to the same epitope as antibody 20D12, or comprises the heavy and/or light chain CDR sequences of antibody 20D12 (SEQ ID NOS: 1 and 2), or is the antibody 20D12, or a fragment thereof.

The anti-Factor D antibodies include human, humanized or chimeric antibodies.

The antibody fragments may, for example, be Fab, Fab', F(ab')$_2$, scFv, (scFv)$_2$, dAb, complementarity determining region (CDR) fragments, linear antibodies, single-chain antibody molecules, minibodies, diabodies, or multispecific antibodies formed from antibody fragments.

Complement-associated eye conditions include, for example, age-related macular degeneration (AMD), choroidal neovascularization (CNV), uveitis, diabetic and other ischemia-related retinopathies, diabetic macular edema, pathological myopia, von Hippel-Lindau disease, histoplasmosis of the eye, Central Retinal Vein Occlusion (CRVO), corneal neovascularization, and retinal neovascularization.

In another aspect, the invention concerns a kit comprising a Factor D antagonist and instructions for administering said antagonist to treat a complement-associated eye condition.

In yet another aspect, the invention concerns the use of a Factor D antagonist in the preparation of a medicament for the treatment of a complement-associated eye condition.

In a further aspect the invention concerns a Factor D antagonist for use in the treatment of a complement-associated eye condition.

BRIEF DESCRIPTION OF THE DRAWINGS

FIG. 4. Heavy and light chain variable domain sequences of murine monoclonal antibody 12D20 (SEQ ID NOS: 1 and 2).

FIG. 6. Amino acid sequence of native human Factor D polypeptide (SEQ ID NO: 3).

FIG. 8. Donor tissues used in the studies.

DETAILED DESCRIPTION OF THE PREFERRED EMBODIMENT

I. Definitions

Figure 1:
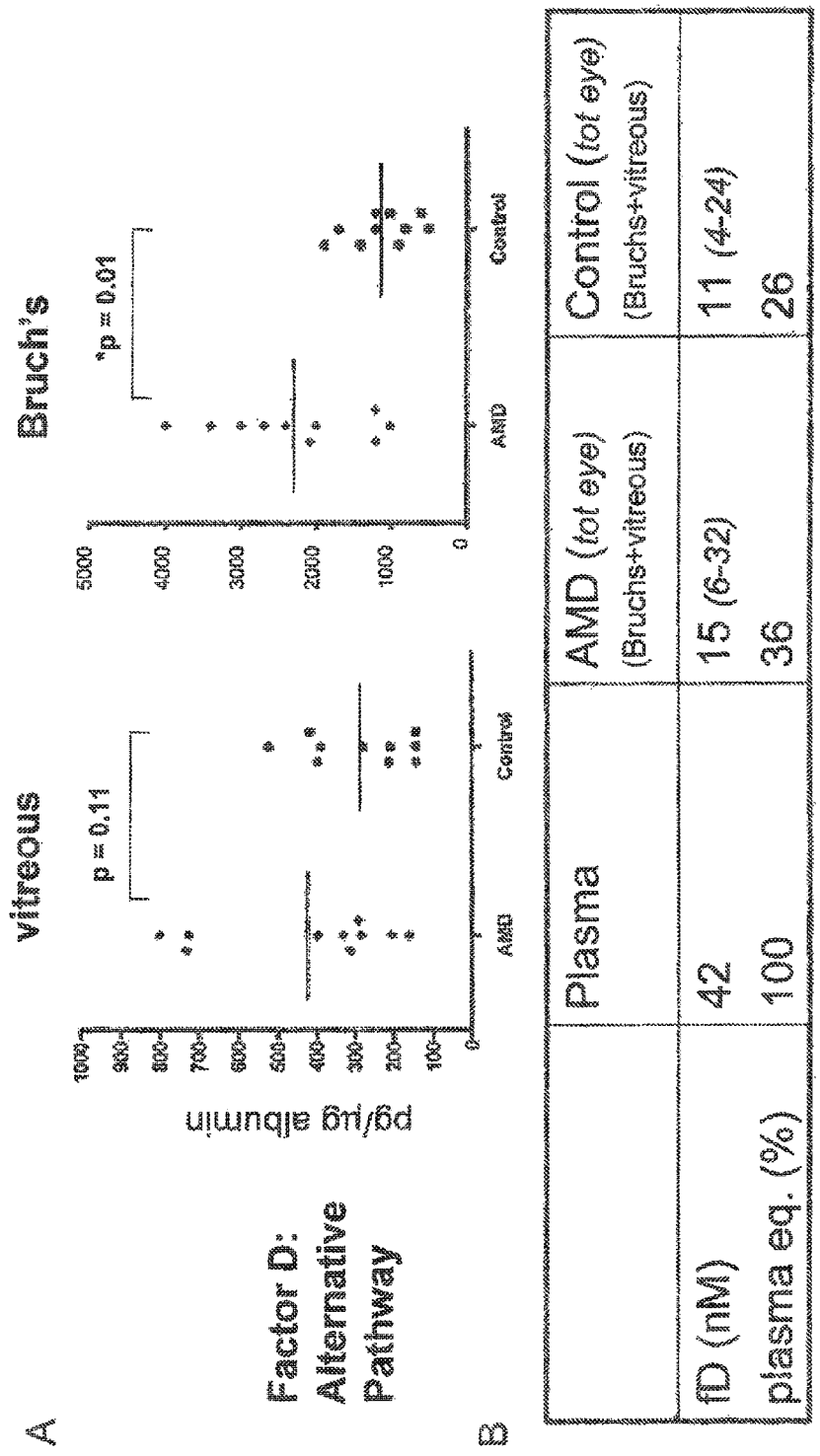
FIG. 1A. Levels of Factor D in vitreous and Bruch's obtained from normal and AMD donor eyes. Factor D levels were measured by a factor D-specific ELISA as described. B: total levels of factor D in the eye were determined by calculating the total contribution of Factor D expressed in Bruch's membrane and the total amount of Factor D found in vitreous.
Figure 2:
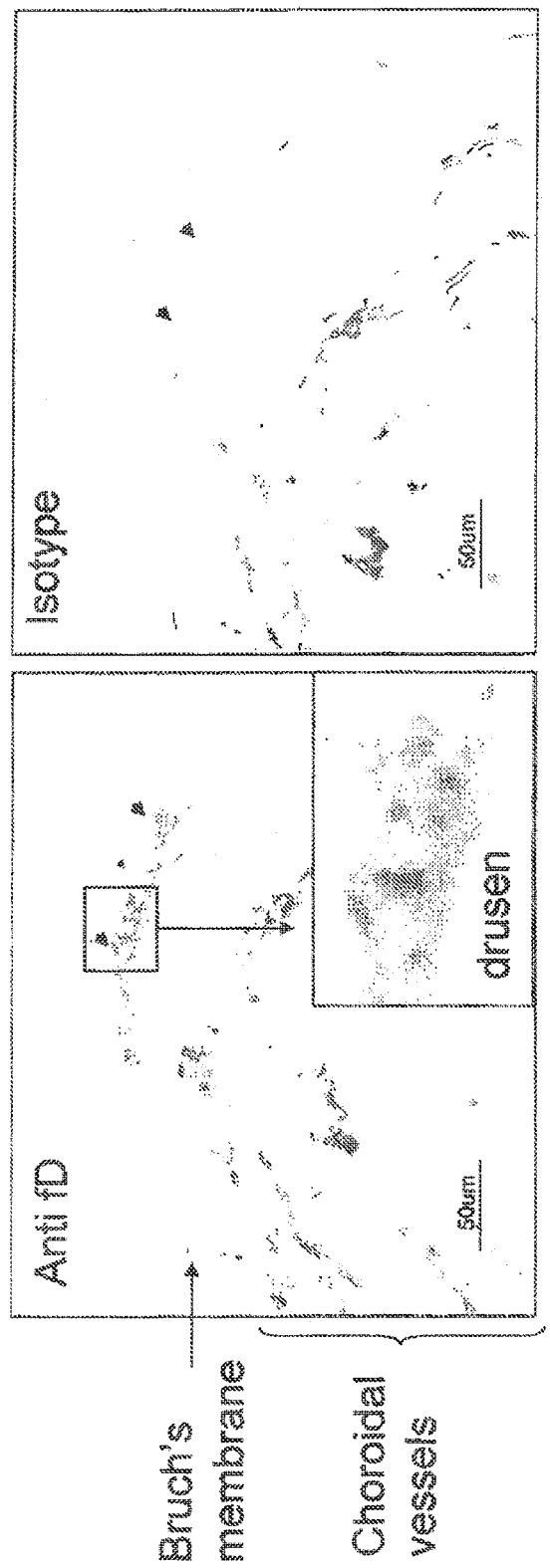
FIG. 2. Factor D immunohistochemistry of a cross-section of a Bruch's membrane from an AMD donor eye. Inset shows staining of Factor D in Druse layered on top of the Bruch's membrane. In addition to Druse, Bruch's membrane and choroid were positive for Factor D.
Figure 3:
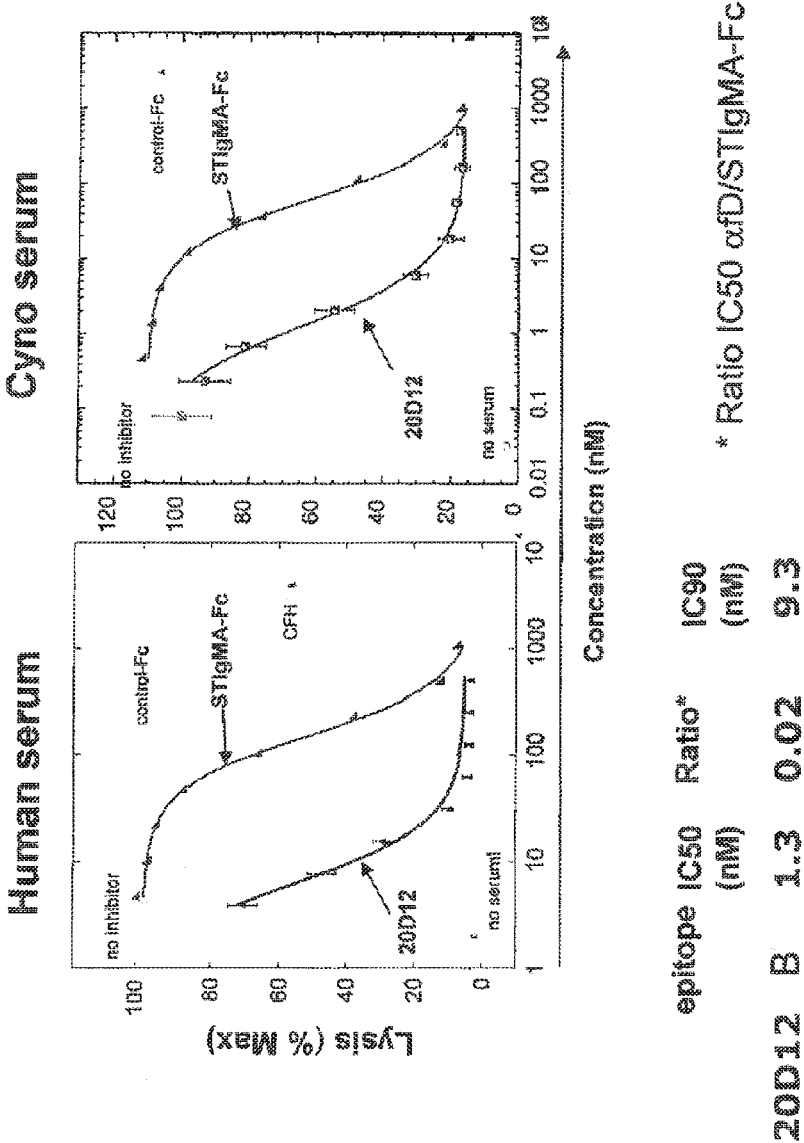
FIG. 3. Characterization of 12D20 in a hemolytic assay selective for the alternative pathway of complement. IC50 values are indicated below and the assay was performed as described in the methods section.

The terms "Factor D" and "complement Factor D" are used interchangeably, and refer to native sequence and variant Factor D polypeptides.

A "native sequence" Factor D, is a polypeptide having the same amino acid sequence as a Factor D polypeptide derived from nature, regardless of its mode of preparation. Thus, native sequence Factor D can be isolated from nature or can be produced by recombinant and/or synthetic means. In addition to a mature Factor D protein, such as a mature human Factor D protein (NM_001928; SEQ ID NO: 3), the term "native sequence Factor D", specifically encompasses naturally-occurring precursor forms of Factor D (e.g., an inactive preprotein, which is proteolytically cleaved to produce the active form), naturally-occurring variant forms (e.g., alternatively spliced forms) and naturally-occurring allelic variants of Factor D, as well as structural conformational variants of Factor D molecules having the same amino acid sequence as a Factor D polypeptide derived from nature. Factor D polypeptides of non-human animals, including higher primates and non-human mammals, are specifically included within this definition.

"Factor D variant" or "complement Factor D variant" means an active Factor D polypeptide as defined below having at least about 80% amino acid sequence identity to a native sequence Factor D polypeptide, such as the native sequence human Factor D polypeptide of SEQ ID NO: 3. Ordinarily, a Factor D variant will have at least about 80% amino acid sequence identity, or at least about 85% amino acid sequence identity, or at least about 90% amino acid sequence identity, or at least about 95% amino acid sequence identity, or at least about 98% amino acid sequence identity, or at least about 99% amino acid sequence identity with the mature human amino acid sequence of SEQ ID NO: 3. Preferably, the highest degree of sequence identity occurs within the active site of Factor D.

The "active site" of Factor D is defined by His-57, Asp-102, and Ser-195 (chymotrypsinogen numbering) in the human Factor D sequence. Factor D has Asp189 (chymotrypsin numbering) at the bottom of the primary specificity pocket and cleaves after an Arg peptide bond. The catalytic triad consists of His-57, Asp-102 and Ser-195. Asp-102 and His57 display atypical conformations compared with other serine proteases (Narayana et al., *J. Mol. Biol.* 235 (1994), 695-708). A unique salt bridge is observed between Asp189 and Arg218 at the bottom of the S1 pocket which elevates loop 214-218 and generates a deep and narrow S1 pocket (Jing et al., *J. Mol. Biol.* 282 (1998) 1061-1081). This loop and several other residues around the active site were shown by mutational analysis to be the key structural determinants of the factor D esterolytic activity (Kim et al., J. Biol. Chem. 270 (1995) 24399-24405). Based on these results, it was proposed that factor D may undergo a conformational change upon binding C3b-bound factor B, resulting in the expression of proteolytic activity (Volanakis and Narayana, *Protein Sci.* 5 (1996) 553-564).

"Percent (%) amino acid sequence identity" is defined as the percentage of amino acid residues in a candidate sequence that are identical with the amino acid residues in a reference Factor D sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

"Percent (%) nucleic acid sequence identity" is defined as the percentage of nucleotides in a candidate sequence that are identical with the nucleotides in a reference Factor D-encoding sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes nucleic acid molecules contained in cells that ordinarily express an encoded polypeptide where, for example, the nucleic acid molecule is in a chromosomal location different from that of natural cells.

An "isolated" Factor D polypeptide-encoding nucleic acid molecule is a nucleic acid molecule that is identified and separated from at least one contaminant nucleic acid molecule with which it is ordinarily associated in the natural source of the Factor D-encoding nucleic acid. An isolated Factor D polypeptide-encoding nucleic acid molecule is other than in the form or setting in which it is found in nature. Isolated Factor D polypeptide-encoding nucleic acid molecules therefore are distinguished from the encoding nucleic acid molecule(s) as they exists in natural cells. However, an isolated Factor D-encoding nucleic acid molecule includes Factor D-encoding nucleic acid molecules contained in cells that ordinarily express Factor D where, for example, the nucleic acid molecule is in a chromosomal location different from that of natural cells.

The term "antagonist" is used in the broadest sense, and includes any molecule that is capable of neutralizing, blocking, partially or fully inhibiting, abrogating, reducing or interfering with a Factor D biological activity. Factor D antagonists include, without limitation, anti-Factor D antibodies and antigen-binding fragments thereof, other binding polypeptides, peptides, and non-peptide small molecules, that bind to Factor D and are capable of neutralizing, blocking, partially or fully inhibiting, abrogating, reducing or interfering with Factor D activities, such as the ability of Factor D to participate in the pathology of a complement-associated eye condition.

A "small molecule" is defined herein to have a molecular weight below about 600, preferably below about 1000 daltons.

"Active" or "activity" or "biological activity" in the context of a Factor D antagonist of the present invention is the ability the antagonize (partially or fully inhibit) a biological activity of Factor D. A preferred biological activity of a Factor D antagonist is the ability to achieve a measurable improvement in the state, e.g. pathology, of a Factor D-associated disease or condition, such as, for example, a complement-associated eye condition. The activity can be determined in in vitro or in vivo tests, including binding assays, using a relevant animal model, or human clinical trials.

The term "complement-associated eye condition" is used in the broadest sense and includes all eye conditions the pathology of which involves complement, including the classical and the alternative pathways, and in particular the alternative pathway of complement. Complement-associated eye conditions include, without limitation, macular degenerative diseases, such as all stages of age-related macular degeneration (AMD), including dry and wet (non-exudative and exudative) forms, choroidal neovascularization (CNV), uveitis, diabetic and other ischemia-related retinopathies, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. A preferred group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In treatment of an immune related disease, a therapeutic agent may directly alter the magnitude of response of a component of the immune response, or render the disease more susceptible to treatment by other therapeutic agents, e.g., antibiotics, antifungals, anti-inflammatory agents, chemotherapeutics, etc.

The "pathology" of a disease, such as a complement-associated eye condition, includes all phenomena that compromise the well-being of the patient. This includes, without limitation, abnormal or uncontrollable cell growth (neutrophilic, eosinophilic, monocytic, lymphocytic cells), antibody production, auto-antibody production, complement production, interference with the normal functioning of neighboring cells, release of cytokines or other secretory products at abnormal levels, suppression or aggravation of any inflammatory or immunological response, infiltration of inflammatory cells (neutrophilic, eosinophilic, monocytic, lymphocytic) into cellular spaces, etc.

The term "mammal" as used herein refers to any animal classified as a mammal, including, without limitation, humans, higher primates, domestic and farm animals, and zoo, sports or pet animals such horses, pigs, cattle, dogs, cats and ferrets, etc. In a preferred embodiment of the invention, the mammal is a human.

Administration "in combination with" one or more further therapeutic agents includes simultaneous (concurrent) and consecutive administration in any order.

"Therapeutically effective amount" is the amount of a "Factor D antagonist" which is required to achieve a measurable improvement in the state, e.g. pathology, of the target disease or condition, such as, for example, a complement-associated eye condition.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 C; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a polypeptide of the invention fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

The term "antibody" is used in the broadest sense and specifically covers, without limitation, single anti-Factor D monoclonal antibodies (including agonist, antagonist, and neutralizing antibodies) and anti-Factor D antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352:624-628 and Marks et al. (1991) J. Mol. Biol. 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) Proc. Natl. Acad. Sci. USA 81:6851-6855).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) Nature 321:522-525; Riechmann et al. (1988) Nature 332:323-329; and Presta (1992) Curr. Op. Struct. Biol. 2:593-596.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In a preferred embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions (CDRs; ie., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) *J. Mol. Biol.* 196:901-917). In some instances, a complementarity determining region can include amino acids from both a CDR region defined according to Kabat and a hypervariable loop. For example, the CDRH1 of the heavy chain of antibody 4D5 includes amino acids 26 to 35.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, eg. NNK, NNS, XYZ, DVK and the like. A "non-random codon set", as used herein, thus refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al. (1999) *J. Mol. Biol.* 296:57-86); Garrard & Henner (1993) *Gene* 128:103). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

The term "antibody fragment" is used herein in the broadest sense and includes, without limitation, Fab, Fab', F(ab')2, scFv, (scFv)2, dAb, and complementarity determining region (CDR) fragments, linear antibodies, single-chain antibody molecules, minibodies, diabodies, and multispecific antibodies formed from antibody fragments.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. F(ab')2 antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the VH and VL domains of antibody, wherein these domains are present in a single polypeptide chain. Generally the Fv polypeptide further comprises a polypeptide linker between the VH and VL domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) Proc. Natl. Acad. Sci. USA 90:6444-6448.

The expression "linear antibodies" refers to the antibodies described in Zapata et al. (1995 Protein Eng, 8(10):1057-1062). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman (1992) Curr. Opin. Struct. Biol. 3:355-362, and references cited therein. In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells (1991) Methods: A companion to Methods in Enzymology 3:205-0216.

A "phagemid" is a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

As used herein, "solvent accessible position" refers to a position of an amino acid residue in the variable regions of the heavy and light chains of a source antibody or antigen binding fragment that is determined, based on structure, ensemble of structures and/or modeled structure of the antibody or antigen binding fragment, as potentially available for solvent access and/or contact with a molecule, such as an antibody-specific antigen. These positions are typically found in the CDRs and on the exterior of the protein. The solvent accessible positions of an antibody or antigen binding fragment, as defined herein, can be determined using any of a number of algorithms known in the art. Preferably, solvent accessible positions are determined using coordinates from a 3-dimensional model of an antibody, preferably using a computer program such as the InsightII program (Accelrys, San Diego, Calif.). Solvent accessible positions can also be determined using algorithms known in the art (e.g., Lee and Richards (1971) J. Mol. Biol. 55, 379 and Connolly (1983) J. Appl. Cryst. 16, 548). Determination of solvent accessible positions can be performed using software suitable for protein modeling and 3-dimensional structural information obtained from an antibody. Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios (1994) Comput. Chem. 18(4): 377-386.

II. Detailed Description

Complement plays a crucial role in the body's defense, and, together with other components of the immune system, protect the individual from pathogens invading the body. However, if not properly activated or controlled, complement can also cause injury to host tissues. Inappropriate activation of complement is involved in the pathogenesis of a variety of diseases, referred to as complement associated diseases or disorders, such as immune complex and autoimmune diseases, and various inflammatory conditions, including complement-mediated inflammatory tissue damage. The pathology of complement-associated diseases varies, and might involve complement activation for a long or short period of time, activation of the whole cascade, only one of the cascades (e.g. classical or alternative pathway), only some components of the cascade, etc. In some diseases complement biological activities of complement fragments result in tissue injury and disease. Accordingly, inhibitors of complement have high therapeutic potential. Selective inhibitors of the alternative pathway would be particularly useful, because clearance of pathogens and other organisms from the blood through the classical pathway will remain intact.

The Factor D antagonists of the present invention are useful for the prevention and treatment of complement-associated eye conditions (all eye conditions and diseases the pathology of which involves complement, including the classical and the alternative pathways, and in particular the alternative pathway of complement), such as, for example, macular degenerative diseases, such as all stages of age-related macular degeneration (AMD), including dry and wet (non-exudative and exudative) forms, choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. A preferred group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

AMD is age-related degeneration of the macula, which is the leading cause of irreversible visual dysfunction in individuals over the age of 60. Two types of AMD exist, non-exudative (dry) and exudative (wet) AMD. The dry, or non-exudative, form involves atrophic and hypertrophic changes in the retinal pigment epithelium (RPE) underlying the central retina (macula) as well as deposits (drusen) on the RPE. Patients with nonexudative AMD can progress to the wet, or exudative, form of AMD, in which abnormal blood vessels called choroidal neovascular membranes (CNVMs) develop under the retina, leak fluid and blood, and ultimately cause a blinding disciform scar in and under the retina. Nonexudative AMD, which is usually a precursor of exudative AMD, is more common. The presentation of nonexudative AMD varies; hard drusen, soft drusen, RPE geographic atrophy, and pigment clumping can be present. Complement components are deposited on the RPE early in AMD and are major constituents of drusen.

The present invention specifically concerns the treatment of high risk AMD, including category 3 and category 4 AMD. Category 3 AMD is characterized by the absence of advanced AMD in both eyes, at least one eye having a visual acuity of 20/32 or better with at least one large druse (e.g. 125 µm), extensive (as measured by drusen area) intermediate drusen, or geographic atrophy (GA) that does not involve the center of the macula, or any combination of these. Category 3 AMD (which is still considered "dry" AMD) has a high risk of cinversion to choroidal neovascularization (CNV).

Category 4 high risk AMD (classified as "wet" AMD) is characterized by a visual acuity of 20/32 or better and no advanced AMD (GA involving the center of the macula or features of choroidal neovascularization) in index eye. The fellow eye is characterized by advanced AMD, or visual acuity less than 20/32 attributable to AMD maculopathy. Typically, high risk AMD, if untreated, rapidly progresses into choroidal neovascularization (CNV), at a rate about 10-30-times higher than the rate of progression for category 1 or 2 (not high risk) AMD.

Factor D antagonists find particular utility in the prevention of the progression of AMD (in particular, category 3 or category 4 AMD) into CNV, and/or the prevention of the development/progression of AMD or CNV in the non- or less effected fellow eye. In this context, the term "prevention" is used in the broadest sense to include, complete or partial blocking and slowing down of the progression of the disease as well as the delay of the unset of the more serious form of the disease. Patients who are at high risk of developing or progressing into high risk (category 4) AMD or CMV especially benefit from this aspect of the invention.

It is known that complement factor H(CFH) polymorphism is associated with the risk of an individual to develop AMD and/or CNV. Muations in CFH can activate complement, which in turn may lead to AMD/CNV. It has been recently reported that complement factor H(CFH) polymorphism accounts for 50% of the attributable risk of AMD (Klein et al., Science 308:385-9 (2005)). A common halpotype in CFH (HF1/CFH) has been found to predispose individuals to age-related macular degeneration (Hageman et al., Proc. Natl. Acad. Sci. USA, 102(2):7227-7232 (2005)). AMD has been segregated as an autosomal-dominant trait, with the disease locus mapping to chromosome 1q25-q31 between markers D15466 and D15413, with a maximum lod score of about 3.20 (Klein et al., Arch Opthalmol. 116(8):1082-9 (1998); Majewski et al., Am. J. Hum. Genet. 73(3):540-50 (2003); Seddon et al., Am. J. Hum. Genet. 73(4):780-90 (2003); Weeks et al., Am. J. Ophthalmol. 132(5):682-92 (2001); Iyengar et al., Am. J. Hum. Genet. 74(1):20-39 (2004)); chromosome 2q3/2q32 between markers D1251391 and D2S1384, with a maximum lode score of 2.32/2.03 (Seddon et al., supra); 3p13, between markers D12S1300 and D1251763, with a maximum lode score of 2.19 (Majewski et al., supra; Schick et al., Am. J. Hum. Genet. 72(6):1412-24 (2003)); 6q14 between markers D6S1056 and DS249 with a maximum lode score of 3.59/3.17 (Kniazeva et al., Am. J. Ophthlmol. 130(2):197-202 (2000)); 9q33, at marker D9S934, with a maximum lode score of 2.06 (Mejwski et al., supra); 10q26 at th marker D10S1230, with a maximum lode score of 3.06 (Majewski et al., supra; Iyengar et al., supra; Kenealy et al., Mol. Vis. 10:57-61 (2004); 17q25 at marker D175928, maximum lode score of 3.16 (Weeks et al., supra); and 22q12 at marker D2251045, maximum lode score of 2.0 (Seddon et al., supra). Accordingly, genetic screening is an important part of identifying patients who are particularly good candidates for preventative treatment, including prevention of the progression of the disease into a more severe form, such as from AMD to CNV.

1. Anti-Factor D Antibodies

The invention herein includes the production and use of anti-Factor D antibodies. Exemplary methods for generating antibodies are described in more detail in the following sections.

Anti-Factor D antibodies are selected using a Factor D antigen derived from a mammalian species. Preferably the antigen is human Factor D. However, Factor Ds from other species such as murine Factor D can also be used as the target antigen. The Factor D antigens from various mammalian species may be isolated from natural sources. In other embodiments, the antigen is produced recombinantly or made using other synthetic methods known in the art.

The antibody selected will normally have a sufficiently strong binding affinity for the Factor D antigen. For example, the antibody may bind human Factor D with a Kd value of no more than about 5 nM, preferably no more than about 2 nM, and more preferably no more than about 500 pM. Antibody affinities may be determined by a surface plasmon resonance based assay (such as the BIAcore assay as described in Examples); enzyme-linked immunoabsorbent assay (ELISA); and competition assays (e.g. RIA's), for example.

Also, the antibody may be subject to other biological activity assays, e.g., in order to evaluate its effectiveness as a therapeutic. Such assays are known in the art and depend on the target antigen and intended use for the antibody. Examples include the HUVEC inhibition assay (as described in the Examples below); tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and in vitro and in vivo assays described below for identifying Factor D antagonists.

To screen for antibodies which bind to a particular epitope on the antigen of interest, a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al. (1995) J. Biol. Chem. 270:1388-1394, can be performed to determine whether the antibody binds an epitope of interest.

In a preferred embodiment, the anti-Factor D antibodies are selected using a unique phage display approach. The approach involves generation of synthetic antibody phage libraries based on single framework template, design of sufficient diversities within variable domains, display of polypeptides having the diversified variable domains, selection of candidate antibodies with high affinity to target Factor D antigen, and isolation of the selected antibodies.

Details of the phage display methods can be found, for example, in WO03/102157 published Dec. 11, 2003.

In one aspect, the antibody libraries can be generated by mutating the solvent accessible and/or highly diverse positions in at least one CDR of an antibody variable domain. Some or all of the CDRs can be mutated using the methods provided herein. In some embodiments, it may be preferable to generate diverse antibody libraries by mutating positions in CDRH1, CDRH2 and CDRH3 to form a single library or by mutating positions in CDRL3 and CDRH3 to form a single library or by mutating positions in CDRL3 and CDRH1, CDRH2 and CDRH3 to form a single library.

A library of antibody variable domains can be generated, for example, having mutations in the solvent accessible and/or highly diverse positions of CDRH1, CDRH2 and CDRH3. Another library can be generated having mutations in CDRL1, CDRL2 and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

Preferably, a library is created by substitution of original amino acids with variant amino acids in the CDRH3 region of the variable region of the heavy chain sequence. The resulting library can contain a plurality of antibody sequences, wherein the sequence diversity is primarily in the CDRH3 region of the heavy chain sequence.

In one aspect, the library is created in the context of the humanized antibody 4D5 sequence, or the sequence of the framework amino acids of the humanized antibody 4D5 sequence. Preferably, the library is created by substitution of at least residues 95-100a of the heavy chain with amino acids encoded by the DVK codon set, wherein the DVK codon set is used to encode a set of variant amino acids for every one of these positions. An example of an oligonucleotide set that is useful for creating these substitutions comprises the sequence $(DVK)_7$. In some embodiments, a library is created by substitution of residues 95-100a with amino acids encoded by both DVK and NNK codon sets. An example of an oligonucleotide set that is useful for creating these substitutions comprises the sequence $(DVK)_6$ (NNK). In another embodiment, a library is created by substitution of at least residues 95-100a with amino acids encoded by both DVK and NNK codon sets. An example of an oligonucleotide set that is useful for creating these substitutions comprises the sequence $(DVK)_5$ (NNK). Another example of an oligonucleotide set that is useful for creating these substitutions comprises the sequence $(NNK)_6$. Other examples of suitable oligonucleotide sequences can be determined by one skilled in the art according to the criteria described herein.

In another embodiment, different CDRH3 designs are utilized to isolate high affinity binders and to isolate binders for a variety of epitopes. The range of lengths of CDRH3 generated in this library is 11 to 13 amino acids, although lengths different from this can also be generated. H3 diversity can be expanded by using NNK, DVK and NVK codon sets, as well as more limited diversity at N and/or C-terminal.

Diversity can also be generated in CDRH1 and CDRH2. The designs of CDR-H1 and H2 diversities follow the strategy of targeting to mimic natural antibodies repertoire as described with modification that focus the diversity more closely matched to the natural diversity than previous design.

For diversity in CDRH3, multiple libraries can be constructed separately with different lengths of H3 and then combined to select for binders to target antigens. The multiple libraries can be pooled and sorted using solid support selection and solution sorting methods as described previously and herein below. Multiple sorting strategies may be employed. For example, one variation involves sorting on target bound to a solid, followed by sorting for a tag that may be present on the fusion polypeptide (eg. anti-gD tag) and followed by another sort on target bound to solid. Alternatively, the libraries can be sorted first on target bound to a solid surface, the eluted binders are then sorted using solution phase binding with decreasing concentrations of target antigen. Utilizing combinations of different sorting methods provides for minimization of selection of only highly expressed sequences and provides for selection of a number of different high affinity clones.

High affinity binders for the target Factor D antigen can be isolated from the libraries. Limiting diversity in the H1/H2 region decreases degeneracy about 104 to 105 fold and allowing more H3 diversity provides for more high affinity binders. Utilizing libraries with different types of diversity in CDRH3 (eg. utilizing DVK or NVT) provides for isolation of binders that may bind to different epitopes of a target antigen.

In another embodiment, a library or libraries with diversity in CDRH1, CDRH2 and CDRH3 regions is generated. In this embodiment, diversity in CDRH3 is generated using a variety of lengths of H3 regions and using primarily codon sets XYZ and NNK or NNS. Libraries can be formed using individual oligonucleotides and pooled or oligonucleotides can be pooled to form a subset of libraries. The libraries of this embodiment can be sorted against target bound to solid. Clones isolated from multiple sorts can be screened for specificity and affinity using ELISA assays. For specificity, the clones can be screened against the desired target antigens as well as other nontarget antigens. Those binders to the target NRP1 antigen can then be screened for affinity in solution binding competition ELISA assay or spot competition assay. High affinity binders can be isolated from the library utilizing XYZ codon sets prepared as described above. These binders can be readily produced as antibodies or antigen binding fragments in high yield in cell culture.

In some embodiments, it may be desirable to generate libraries with a greater diversity in lengths of CDRH3 region. For example, it may be desirable to generate libraries with CDRH3 regions ranging from about 7 to 19 amino acids.

High affinity binders isolated from the libraries of these embodiments are readily produced in bacterial and eukaryotic cell culture in high yield. The vectors can be designed to readily remove sequences such as gD tags, viral coat protein component sequence, and/or to add in constant region sequences to provide for production of full length antibodies or antigen binding fragments in high yield.

A library with mutations in CDRH3 can be combined with a library containing variant versions of other CDRs, for example CDRL1, CDRL2, CDRL3, CDRH1 and/or CDRH2. Thus, for example, in one embodiment, a CDRH3 library is combined with a CDRL3 library created in the context of the humanized 4D5 antibody sequence with variant amino acids at positions 28, 29, 30, 31, and/or 32 using predetermined codon sets. In another embodiment, a library with mutations to the CDRH3 can be combined with a library comprising variant CDRH1 and/or CDRH2 heavy chain variable domains. In one embodiment, the CDRH1 library is created with the humanized antibody 4D5 sequence with variant amino acids at positions 28, 30, 31, 32 and 33. A CDRH2 library may be created with the sequence of humanized antibody 4D5 with variant amino acids at positions 50, 52, 53, 54, 56 and 58 using the predetermined codon sets.

Figure 5:
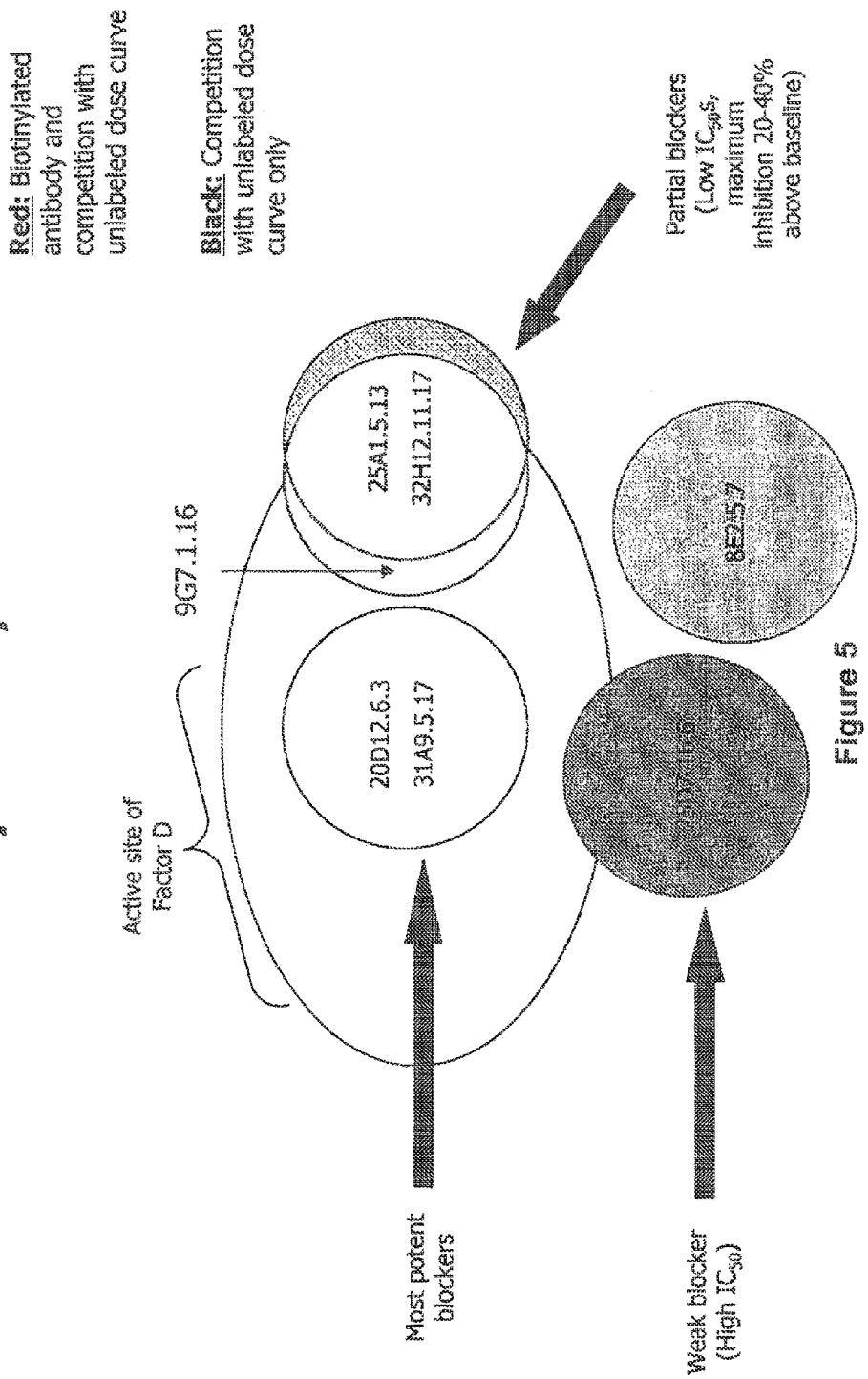
FIG. 5. Epitope mapping of the various anti-Factor D antibodies. Indicated are their relative potencies in the hemolysis assay.
Figure 7:
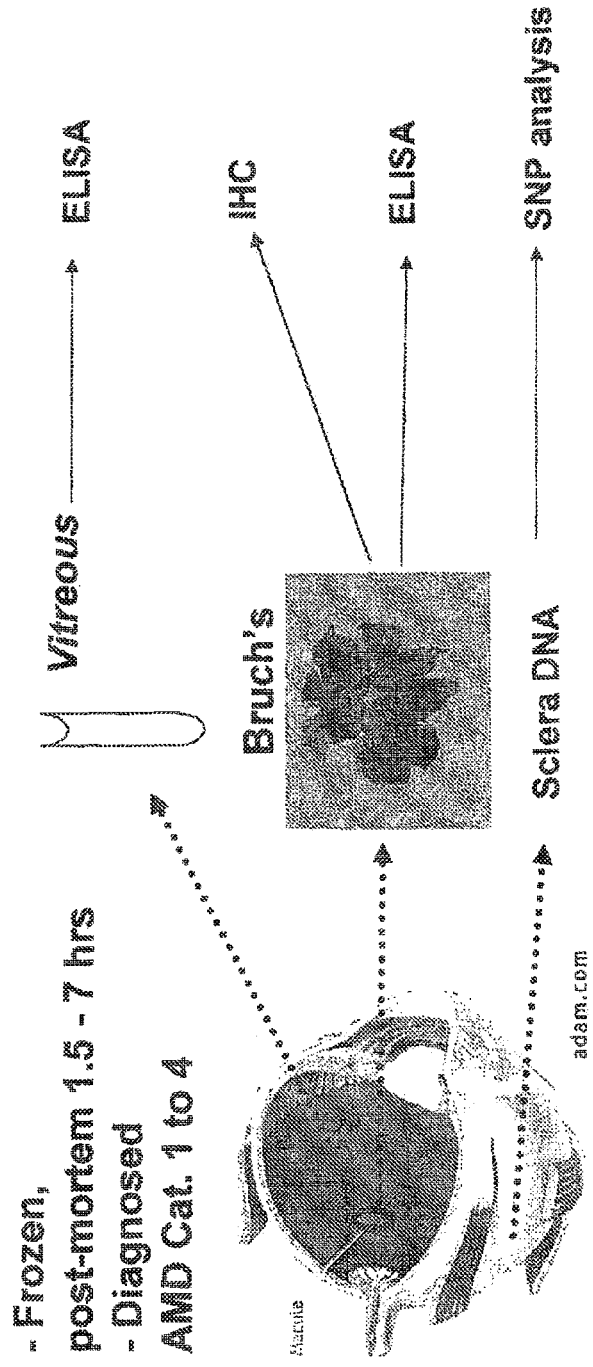
FIG. 7. Analysis of complement components in AMD.

The anti-Factor D antibody generated from phage libraries can be further modified to generate antibody mutants with improved physical, chemical and or biological properties over the parent antibody. Where the assay used is a biological activity assay, the antibody mutant preferably has a biological activity in the assay of choice which is at least about 10 fold better, preferably at least about 20 fold better, more preferably at least about 50 fold better, and sometimes at least about 100 fold or 200 fold better, than the biological activity of the parent antibody in that assay. For example, an anti-Factor D antibody mutant preferably has a binding affinity for NRP which is at least about 10 fold stronger, preferably at least about 20 fold stronger, more preferably at least about 50 fold stronger, and sometimes at least about 100 fold or 200 fold stronger, than the binding affinity of the parent anti-Factor D antiodies, such as, any of the antibodies shown I FIG. 5, and in particular, antibody 20D12.

To generate the antibody mutant, one or more amino acid alterations (e.g. substitutions) are introduced in one or more of the hypervariable regions of the parent antibody. Alternatively, or in addition, one or more alterations (e.g. substitutions) of framework region residues may be introduced in the parent antibody where these result in an improvement in the binding affinity of the antibody mutant for the antigen from the second mammalian species. Examples of framework region residues to modify include those which non-covalently bind antigen directly (Amit et al. (1986) Science 233:747-

753); interact with/effect the conformation of a CDR (Chothia et al. (1987) J. Mol. Biol. 196:901-917); and/or participate in the VL-VH interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alteration(s).

The hypervariable region residues which are altered may be changed randomly, especially where the starting binding affinity of the parent antibody is such that such randomly produced antibody mutants can be readily screened.

One useful procedure for generating such antibody mutants is called "alanine scanning mutagenesis" (Cunningham and Wells (1989) *Science* 244:1081-1085). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. The ala-mutants produced this way are screened for their biological activity as described herein.

Normally one would start with a conservative substitution such as those shown below under the heading of "preferred substitutions". If such substitutions result in a change in biological activity (e.g. binding affinity), then more substantial changes, denominated "exemplary substitutions" in the following table, or as further described below in reference to amino acid classes, are introduced and the products screened. Preferred substitutions are listed in the table below.

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Even more substantial modifications in the antibodies biological properties are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr, asn, gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

In another embodiment, the sites selected for modification are affinity matured using phage display (see above).

Nucleic acid molecules encoding amino acid sequence mutants are prepared by a variety of methods known in the art. These methods include, but are not limited to, oligonucleotide-mediated (or site-directed) mutagenesis, PCR mutagenesis, and cassette mutagenesis of an earlier prepared mutant or a non-mutant version of the parent antibody. The preferred method for making mutants is site directed mutagenesis (see, e.g., Kunkel (1985) Proc. Natl. Acad. Sci. USA 82:488).

In certain embodiments, the antibody mutant will only have a single hypervariable region residue substituted. In other embodiments, two or more of the hypervariable region residues of the parent antibody will have been substituted, e.g. from about two to about ten hypervariable region substitutions.

Ordinarily, the antibody mutant with improved biological properties will have an amino acid sequence having at least 75% amino acid sequence identity or similarity with the amino acid sequence of either the heavy or light chain variable domain of the parent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties, see above) with the parent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

Following production of the antibody mutant, the biological activity of that molecule relative to the parent antibody is determined. As noted above, this may involve determining the binding affinity and/or other biological activities of the antibody. In a preferred embodiment of the invention, a panel of antibody mutants is prepared and screened for binding affinity for the antigen such as NRP1 or a fragment thereof. One or more of the antibody mutants selected from this initial screen are optionally subjected to one or more further biological activity assays to confirm that the antibody mutant(s) with enhanced binding affinity are indeed useful, e.g. for preclinical studies.

The antibody mutant(s) so selected may be subjected to further modifications, oftentimes depending on the intended use of the antibody. Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residue not involved in maintaining the proper conformation of the antibody mutant also may be substituted, generally with serine, to improve the oxidative stability of the molecule and prevent aberrant cross linking Conversely, cysteine bond(s) may be added to the antibody to improve its stability (particularly where the antibody is an antibody fragment such as an Fv fragment). Another type of amino acid mutant has an altered glycosylation pattern. This may be achieved by deleting one or more carbohydrate moieties found in the antibody, and/or adding one or more glycosylation sites that are not present in the antibody. Glycosylation of antibodies is typically either N-linked or O-linked N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The anti-Factor D antibodies of the invention can be produced recombinantly, using techniques and materials readily obtainable.

For recombinant production of an anti-Factor D antibody, the nucleic acid encoding it is isolated and inserted into a replicable vector for further cloning (amplification of the DNA) or for expression. DNA encoding the antibody is readily isolated or synthethized using conventional procedures (e.g., by using oligonucleotide probes that are capable of binding specifically to DNAs encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al. (1979) Nature 282:39). The trp1 gene provides a selection marker for a mutant strain of yeast lacking the ability to grow in tryptophan, for example, ATCC No. 44076 or PEP4-1. Jones (1977) Genetics 85:12. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K.*

*lactis.* Van den Berg (1990) *Bio/Technology* 8:135. Stable multi-copy expression vectors for secretion of mature recombinant human serum albumin by industrial strains of *Kluyveromyces* have also been disclosed. Fleer et al. (1991) *Bio/Technology* 9:968-975.

(iv) Promoter Component

Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al. (1982) *Nature* 297:598-601 on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv (1982) *Nature* 297:17-18 on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis*(e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera fru-*

*giperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al. (1977) *J. Gen Virol.* 36:59); baby hamster kidney cells (BHK, ATCC CCL 10); Chinese hamster ovary cells/-DHFR (CHO, Urlaub et al. (1980) *Proc. Natl. Acad. Sci. USA* 77:4216); mouse sertoli cells (TM4, Mather (1980) *Biol. Reprod.* 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al. (1982) *Annals N. Y. Acad. Sci.* 383:44-68); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al. (1979) *Meth. Enz.* 58:44, Barnes et al. (1980) *Anal. Biochem.* 102:255, U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al. (1992) *Bio/Technology* 10:163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al. (1983) *J. Immunol. Meth.* 62:1-13). Protein G is recommended for all mouse isotypes and for human γ3 (Guss et al. (1986) *EMBO J.* 5:15671575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

2. Screening Assays and Animal Models for Identifying Factor D Antagonists

Factor D antagonists can be evaluated in a variety of cell-based assays and animal models of complement-associated diseases or disorders.

Thus, for example, recombinant (transgenic) animal models can be engineered by introducing the coding portion of the genes of interest into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and other monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82, 6148-615 [1985]); gene targeting in embryonic stem cells (Thompson et al., *Cell* 56, 313-321 [1989]); electroporation of embryos (Lo, *Mol. Cell. Biol.* 3, 1803-1814 [1983]); sperm-mediated gene transfer (Lavitrano et al., *Cell* 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89, 623-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with a candidate Factor D antagonist to determine the extent of effects on complement and complement activation, including the classical and alternative pathways, or T cell proliferation. In these experiments, blocking antibodies which bind to the polypeptide of the invention, are administered to the animal and the biological effect of interest is monitored.

Alternatively, "knock out" animals can be constructed which have a defective or altered gene encoding Factor D, as a result of homologous recombination between the endogenous gene encoding the Factor D polypeptide and altered genomic DNA encoding the same polypeptide introduced into an embryonic cell of the animal. For example, cDNA encoding Factor D can be used to clone genomic DNA encoding Factor D in accordance with established techniques. A portion of the genomic DNA encoding Factor D can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the Factor D polypeptide.

Thus, the biological activity of potential Factor D antagonists can be further studied in murine Factor D knock-out mice.

An animal model of age-related macular degeneration (AMD) consists of mice with a null mutation in Ccl-2 or Ccr-2 gnes. These mice develop cardinal features of AMD, including accumulation of lipofuscin in and drusen beneath the retinal pigmented epithelium (RPE), photoreceptor atrophy and choroidal neovascularization (CNV). These features develop beyond 6 months of age. Candidate Factor D antagonists can be tested for the formation of drusen, photoreceptor atrophy and choroidal neovascularization.

3. Pharmaceutical Compositions

The Factor D antagonists of the present invention, including anti-Factor D antibodies and other molecules identified by the screening assays disclosed above, can be administered for the treatment of complement-associates eye conditions in the form of pharmaceutical compositions.

Therapeutic formulations of a Factor D antagonist of the invention, are prepared for storage by mixing the active molecule having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Lipofections or liposomes can also be used to deliver the polypeptide, antibody, or an antibody fragment, into cells. Where antibody fragments are used, the smallest fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., *Proc. Natl. Acad. Sci. USA* 90, 7889-7893 [1993]).

The active molecules may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The compounds of the invention for prevention or treatment of an ocular disease or condition are typically administered by ocular, intraocular, and/or intravitreal injection. Other methods administration by also be used, which includes but is not limited to, topical, parenteral, subcutaneous, intraperitoneal, intrapulmonary, intranasal, and intralesional administration. Parenteral infusions include intramuscular, intravenous, intraarterial, intraperitoneal, or subcutaneous administration.

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitrial injections are usually repeated at intervals which depend on the patient's condition, and the properties and half-life of the drug delivered. For intraocular (e.g. intravitreal) penetration, usually molecules of smaller size are preferred.

The efficacy of the treatment of complement-associated eye conditions, such as AMD or CNV, can be measured by various endpoints commonly used in evaluating intraocular diseases. For example, vision loss can be assessed. Vision loss can be evaluated by, but not limited to, e.g., measuring by the mean change in best correction visual acuity (BCVA) from baseline to a desired time point (e.g., where the BCVA is based on Early Treatment Diabetic Retinopathy Study (ETDRS) visual acuity chart and assessment at a test distance of 4 meters), measuring the proportion of subjects who lose fewer than 15 letters in visual acuity at a desired time point compared to baseline, measuring the proportion of subjects who gain greater than or equal to 15 letters in visual acuity at a desired time point compared to baseline, measuring the proportion of subjects with a visual-acuity Snellen equivalent of 20/2000 or worse at a desired time point, measuring the NEI Visual Functioning Questionnaire, measuring the size of CNV and amount of leakage of CNV at a desired time point, e.g., by fluorescein angiography, etc. Ocular assessments can be done, e.g., which include, but are not limited to, e.g., performing eye exam, measuring intraocular pressure, assessing visual acuity, measuring slitlamp pressure, assessing intraocular inflammation, etc.

The following examples are offered for illustrative purposes only, and are not intended to limit the scope of the present invention in any way.

All patent and literature references cited in the present specification are hereby expressly incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, 10801 University Boulevard, Manassas, Va. 20110-2209.

Example 1

Preparation and Testing of Anti-Factor D Antibody

Methods:

Preparation of Vitreous Fluid and Bruch's Membrane for Protein Analysis

Human AMD and non-AMD cadaver eyes were thawed and the anterior segment removed along with the vitreous, retina and RPE. The vitreous was collected in microtubes, frozen on dry ice and stored at −70 C until further processing. The Bruch's membrane-choroid layer was stripped from the posterior half-globe (Crabb, J. W. et al., *Proc Natl Acad Sci USA.*, 99:14682-7 (2002)) and either 4 mm or 6 mm trephined samples were isolated from the macular and surrounding central region for subsequent analysis. See FIG. 8 showing the Bruch's membrane preparations, age, gender, AMD stage, dissection notes and amounts used for proteomic analysis. One trephined sample, 4 mm diameter, was used for analysis of complement Factor D protein levels. The sample was sonicated for 10 min in Assay Diluent (PBS/0.5% BAS/0.5% Tween-20) and the soluble and insoluble fractions separted by centrifugation for 10 min at 5000 rpm. The soluble fraction was used of the ELISA assays.

Generation of Monoclonal Antibodies to Human Factor D

Monoclonal antibodies to human factor D were generated by injecting 2 µg of factor D (Comptech, Taylor, Tex.) in monophosphoryl lipid A/trehalose dicorynomycolate adjuvant (Corixa, Hamilton, Mont.) in the footpads of Balb/c mice, 11 times. Popliteal lymph nodes from mice were fused with P3X63Ag.U.1 myeloma cells. Hybridoma cells were screened against murine factor D for binding affinity. Cell lines producing antibodies were cloned by limiting dilution.

Hemolysis Assays

For determining alternative pathway activity, rabbit erythrocytes (Er, Colorado Serum) were washed 3× in GVB and resuspended to $2 \times 10^9$/ml. Inhibitors (50 µl) and 20 µl of Er suspension were mixed 1:1 with GVB/0.1M EGTA/0.1M $MgCl_2$. Complement activation was initiated by the addition of C1q-depleted human serum (Quidel; 30 µl diluted 1:3 in GVB). After a 30 minute incubation at room temperature, 200

μl GVB/10 mM EDTA were added to stop the reaction and samples were centrifuged for 5 min at 500 g. Hemolysis was determined in 200 μl supernatant by measuring absorbance at 412 nm Data were expressed as % of hemolysis induced in the absence of the inhibitor. To determine the effect of Factor D antibody on the classical pathway of complement, a similar procedure was followed except that Er were replaced with IgM-coated sheep erythrocytes (E-IgM, CompTech) and the assay was performed in factor B deficient human serum in GVB++.

Human Factor D ELISA

Anti-human complement Factor D goat polyclonal antibody (pAb) (R&D Systems, Minneapolis, Minn.) was diluted to 1 μg/mL in phosphate buffered saline (PBS) and coated on ELISA plates (384-well, high-bind plates, Greiner Bio One through VWR International, Bridgepoint, N.J.) during an overnight incubation at 4° C. After washing 3 times with wash buffer (PBS/0.05% Tween-20), the plates were blocked with PBS/0.5% bovine serum albumin (BSA) for 1 to 2 hours. This and all other incubations were performed at room temperature on an orbital shaker. Human vitreous fluid and Bruch's membrane lysate samples were diluted using Assay Diluent (PBS/0.5% BSA/0.5% Tween-20). Using the same buffer, the serial dilutions were prepared of the factor D (Complement Technology, Inc., Tyler, Tex.) standard curve (15.6 pg/mL-1, 000 pg/mL). Frozen control samples pre-diluted to quantitate at the high, mid, and low regions of the standard curve were thawed. After the blocking step, the plates were washed and the samples, standards, and controls were added and incubated for 2 hours. The plates were washed, and biotinylated anti-human Factor D monoclonal antibody 9G7.1.16 was diluted to 62.5 ng/mL and added to the plates for a 1 to 2 hour incubation. Streptavidin-horse radish peroxidase (SA-HRP) (Amersham Pharmacia Biotech, Piscataway, N.J.) was diluted 1/10,000 in Assay Diluent and added to the washed plates. Following a 30 minute incubation and a final wash step, tetramethyl benzidine (TMB) (Kirkegaard & Perry Laboratories, Gaithersburg, Md.) was added and color was developed for 5 to 7 minutes. Finally, the reaction was stopped by adding 1M phosphoric acid. The optical density was obtained using a microplate reader (450 nm, 650 nm reference), and the sample concentrations were calculated from 4-parameter fits of the standard curves. The minimum quantifiable concentrations of factor D in human vitreous fluid and Bruch's membrane lysate samples were 780 pg/mL (1/50 minimum dilution) and 156 pg/mL (1/10 minimum dilution), respectively.

Immunohistochemistry

Bruch's membrane samples were frozen in OCT compound, and 7 μm sections cut on a cryomicrotome. Immunostaining. Sections were fixed in Acetone for 5 minutes after sectioning and stored at −80 C until ready to stain. Frozen slides were rinsed in PBS 2 times, followed by 2 rinses Tris-Buffered Saline containing 0.1% Tween (TBST). Endogenous avidin and biotin was blocked with Vector Avidin Biotin Blocking Kit (SP-2001) at room temperature follow manufacturers directions. Sections were rinsed in TBST, 2 changes, 5 minutes each and endogenous immunoglobulins were blocked with 10% Horse serum in 3% BSA/PBS for 30 minutes at room temperature. Sections were incubated with anti-human Factor-D (9G7.1.16) antibody diluted to 10 μg/ml in 10% Horse serum for 60 minutes at room temperature. Naive Mouse IgG2a @ 10 μg/ml (Pharmingen) was used as negative control. Following rinsing in TBST, 2 changes, 5 minutes each, sectiones were incubated with biotinylated Horse anti-Mouse antibody (Vector) diluted to 2.5 μg/ml (1:200) in Horse serum for 30 minutes. Sections were rinsed in TBST, 2 changes, 5 minutes each and incubated with Vectastain ABC-AP Elite Reagent for 30 minutes at room temperature, rinsed in TBST (2 changes, 5 minutes each) and incubated in freshly prepared Vector Red solution Vector Red was prepared as follows: For 200 mM Tris HCl, dilute 1 M Tris HCl 1:5 in dH2O (1 part Tris HCl and 4 Parts dH2O). Mix 1 drop of Levamisole in every 5 ml of 200 mM solution of freshly prepared Tris HCl.Mix 2 drops of Reagents 1, 2 and 3 from Vector Red kit individually in every 5 ml of 200 mM Tris HCl-Levamisole solution. Use within 5-10 minutes of addition of Reagent 3 from Vector Red kit. Sectiones were rinsed in H20 and counterstained with Mayer's hematoxylin by dipping in hematoxylin for 10-15 dips (20-30 seconds), rinsed with water and blue, and rinsed well in running water for 5 minutes to wash-off bluing reagent. Sections were mounted with Crystal Mount solution and let dry overnight. The dried Crystal mount covered slides were dipped in Xylenes and coverslipped using permamount mounting medium.

Cloning of the Heavy- and Light Chain of 20D12

Total RNA was extracted from hybridoma cells producing the mouse anti-human Factor D monoclonal 20D12, using RNeasy Mini Kit (Qiagen, Germany). The variable light (VL) and variable heavy (VH) domains were amplified using RT-PCR with the following degenerate primers:

```
Light chain (LC) forward:
                                           (SEQ ID NO: 4)
5'GATCGATATCGTRATGACHCARTCTCA3'

Light chain reverse:
                                           (SEQ ID NO: 5)
5'TTTDAKYTCCAGCTTGGTACC3'

Heavy chain (HC) forward:
                                           (SEQ ID NO: 6)
5'GATCCGTACGCTCAGGTYCARYTGCARCARTCTGG3'

Heavy chain reverse:
                                           (SEQ ID NO: 7)
5'ACAGTGGGCCCTTGGTGGAGGCTGMRGAGACDGTGASHRDRGT3'
```

The forward primers were specific for the N-terminal amino acid sequence of the VL and VH region. Respectively, the LC and HC reverse primers were designed to anneal to a region in the constant light (CL) and constant heavy domain 1 (CH1), which is highly conserved across species.

Amplified VL was cloned into a pRK mammalian cell expression vector (Shields et al., J Biol Chem 2000; 276: 6591-604), containing the human kappa constant domain. Amplified VH was inserted to a pRK mammalian cell expression vector encoding the full-length human IgG1 constant domain. Thus, 20D12 was reformatted to a mouse-human IgG1 chimera.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents.

Indeed, various modifications of the invention in addition to those shown and described herein will become apparent to those skilled in the art from the foregoing description and fall within the scope of the appended claims.

What is claimed is:

1. An isolated polynucleotide encoding an anti-Factor D antibody, or a binding fragment thereof, wherein said antibody or said binding fragment comprises the Complementarity Determining Regions (CDRs) of antibody 20D12 light and heavy chain variable domains (SEQ ID NOS: 1 and 2, respectively), and wherein
the light chain CDR1 sequence comprises amino acid residues 24-34, the light chain CDR2 sequence comprises amino acid residues 50-56, and the light chain CDR3 sequence comprises amino acid residues 89-97 of SEQ ID NO: 1, and
the heavy chain CDR1 sequence comprises amino acid residues 31-35, the heavy chain CDR2 sequence comprises amino acid residues 50-65, and the heavy chain CDR3 sequence comprises amino acid residues 95-102 of SEQ ID NO: 2.

2. The polynucleotide of claim 1, wherein said antibody comprises the light and heavy chain variable domains of antibody 20D12 (SEQ ID NOS: 1 and 2, respectively).

3. The polynucleotide of claim 1, wherein said binding fragment is selected from the group consisting of Fab, Fab', F(ab')$_2$, scFv, (scFv)$_2$, dAb, complementarity determining regions (CDRs), linear antibodies, single-chain antibody molecules, minibodies, diabodies, and multispecific antibodies comprising antigen-binding fragments.

4. The polynucleotide of claim 3, wherein said binding fragment is selected from the group consisting of a Fab, Fab', F(ab')$_2$, scFv, or (scFv)$_2$ fragment.

5. A vector comprising the polynucleotide of any one of claims 1-4.

6. A host cell comprising the vector of claim 5.

7. The host cell of claim 6, wherein the host cell is a bacteria, yeast, insect, or mammalian cell.

8. The host cell of claim 7, wherein the host cell is a CHO cell.

9. A method of making an anti-Factor D antibody, wherein the method comprises a) culturing the host cell of claim 6 under conditions suitable for expression of the polynucleotide encoding the antibody, and b) isolating the antibody.

* * * * *

SEQUENCE LISTING

<160> NUMBER OF SEQ ID NOS: 7

<210> SEQ ID NO 1
<211> LENGTH: 233
<212> TYPE: PRT
<213> ORGANISM: Mus musculus

<400> SEQUENCE: 1

Met Gly Trp Ser Cys Ile Ile Leu Phe Leu Val Ala Thr Ala Thr Gly
1               5                   10                  15

Val His Ser Asp Ile Val Met Thr Gln Ser Gln Lys Phe Met Ser Thr
            20                  25                  30

Ser Val Gly Asp Arg Val Ser Val Thr Cys Lys Ala Ser Gln Asn Val
        35                  40                  45

Asp Thr Asp Val Ala Trp Phe Gln Gln Lys Pro Gly Gln Ser Pro Arg
    50                  55                  60

Gly Leu Ile Tyr Ser Ala Ser Ser Arg Tyr Ser Gly Val Pro Asp Arg
65                  70                  75                  80

Phe Thr Gly Ser Gly Ser Gly Thr Asp Phe Thr Leu Thr Ile Ser Asn
                85                  90                  95

Val Gln Ser Glu Asp Leu Ala Glu Tyr Phe Cys Gln Gln Tyr Asn Asn
            100                 105                 110

Tyr Pro Leu Thr Phe Gly Ser Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 2
<211> LENGTH: 464
<212> TYPE: PRT
<213> ORGANISM: Mus musculus

<400> SEQUENCE: 2

Met Gly Trp Ser Cys Ile Ile Leu Phe Leu Val Ala Thr Ala Thr Gly
1               5                   10                  15

Ala Tyr Ala Gln Val Gln Leu Gln Gln Ser Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Tyr Met Tyr Trp Val Lys Glu Arg Pro Gly Gln Gly Leu
    50                  55                  60

Glu Trp Ile Gly Glu Ile Asn Pro Thr Asn Gly Gly Thr Asn Phe Asn
65                  70                  75                  80

```
Glu Lys Phe Lys Ser Lys Ala Thr Leu Thr Val Asp Thr Ser Ser Asn
                 85                  90                  95
Thr Ala Tyr Met Gln Leu Ser Ser Leu Thr Ser Glu Asp Ser Ala Val
            100                 105                 110
Tyr Tyr Cys Ala Arg Glu Gly Gly Phe Ala Tyr Trp Gly Gln Gly Thr
        115                 120                 125
Leu Val Thr Val Ser Ala Ala Ser Thr Lys Gly Pro Ser Val Phe Pro
    130                 135                 140
Leu Ala Pro Ser Ser Lys Ser Thr Ser Gly Gly Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Ser Leu Gly Thr Gln Thr Tyr Ile Cys Asn Val Asn His Lys Pro Ser
    210                 215                 220
Asn Thr Lys Val Asp Lys Lys Val Glu Pro Lys Ser Cys Asp Lys Thr
225                 230                 235                 240
His Thr Cys Pro Pro Cys Pro Ala Pro Glu Leu Leu Gly Gly Pro Ser
                245                 250                 255
Val Phe Leu Phe Pro Pro Lys Pro Lys Asp Thr Leu Met Ile Ser Arg
            260                 265                 270
Thr Pro Glu Val Thr Cys Val Val Val Asp Val Ser His Glu Asp Pro
        275                 280                 285
Glu Val Lys Phe Asn Trp Tyr Val Asp Gly Val Glu Val His Asn Ala
    290                 295                 300
Lys Thr Lys Pro Arg Glu Glu Gln Tyr Asn Ser Thr Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Ala Leu Pro Ala Pro Ile Glu Lys Thr
            340                 345                 350
Ile Ser Lys Ala Lys Gly Gln Pro Arg Glu Pro Gln Val Tyr Thr Leu
        355                 360                 365
Pro Pro Ser Arg Glu Glu Met Thr Lys Asn Gln Val Ser Leu Thr Cys
    370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Tyr Ser Lys Leu Thr Val Asp Lys Ser
            420                 425                 430
Arg Trp Gln Gln Gly Asn Val Phe Ser Cys Ser Val Met His Glu Ala
        435                 440                 445
Leu His Asn His Tyr Thr Gln Lys Ser Leu Ser Leu Ser Pro Gly Lys
    450                 455                 460

<210> SEQ ID NO 3
<211> LENGTH: 259
<212> TYPE: PRT
<213> ORGANISM: Homo sapiens

<400> SEQUENCE: 3
```

```
Met His Ser Ser Val Tyr Phe Val Ala Leu Val Ile Leu Gly Ala Ala
 1               5                  10                  15

Val Cys Ala Ala Gln Pro Arg Gly Arg Ile Leu Gly Gly Gln Glu Ala
             20                  25                  30

Ala Ala His Ala Arg Pro Tyr Met Ala Ser Val Gln Val Asn Gly Thr
         35                  40                  45

His Val Cys Gly Gly Thr Leu Leu Asp Glu Gln Trp Val Leu Ser Ala
 50                  55                  60

Ala His Cys Met Asp Gly Val Thr Asp Asp Ser Val Gln Val Leu
 65                  70                  75                  80

Leu Gly Ala His Ser Leu Ser Ala Pro Glu Pro Tyr Lys Arg Trp Tyr
                 85                  90                  95

Asp Val Gln Ser Val Val Pro His Pro Gly Ser Arg Pro Asp Ser Leu
             100                 105                 110

Glu Asp Asp Leu Ile Leu Phe Lys Leu Ser Gln Asn Ala Ser Leu Gly
             115                 120                 125

Pro His Val Arg Pro Leu Pro Leu Gln Tyr Glu Asp Lys Glu Val Glu
         130                 135                 140

Pro Gly Thr Leu Cys Asp Val Ala Gly Trp Gly Val Val Thr His Ala
145                 150                 155                 160

Gly Arg Arg Pro Asp Val Leu His Gln Leu Arg Val Ser Ile Met Asn
                 165                 170                 175

Arg Thr Thr Cys Asn Leu Arg Thr Tyr His Asp Gly Val Val Thr Ile
             180                 185                 190

Asn Met Met Cys Ala Glu Ser Asn Arg Arg Asp Thr Cys Arg Gly Asp
             195                 200                 205

Ser Gly Ser Pro Leu Val Cys Gly Asp Ala Val Glu Gly Val Val Thr
210                 215                 220

Trp Gly Ser Arg Val Cys Gly Asn Gly Lys Lys Pro Gly Val Tyr Thr
225                 230                 235                 240

Arg Val Ser Ser Tyr Arg Met Trp Ile Glu Asn Ile Thr Asn Gly Asn
                 245                 250                 255

Met Thr Ser

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatcgatatc gtratgachc artctca                                      27

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttdakytcc agcttggtac c                                            21

<210> SEQ ID NO 6
<211> LENGTH: 35
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 6
gatccgtacg ctcaggtyca rytgcarcar tctgg                                35

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acagtgggcc cttggtggag gctgmrgaga cdgtgashrd rgt                       43
```